United States Patent [19]
Chang et al.

[11] Patent Number: 5,866,129
[45] Date of Patent: Feb. 2, 1999

[54] METHOD OF PRODUCING AN ANTIBODY WITH A PEPTIDE CORRESPONDING TO MEMBRANE-BOUND IGA

[75] Inventors: Tse Wen Chang; Nancy T. Chang, both of Houston, Tex.

[73] Assignee: Tanox Biosystems, Inc., Houston, Tex.

[21] Appl. No.: 785,565

[22] Filed: Nov. 4, 1991

Related U.S. Application Data

[60] Division of Ser. No. 455,080, Dec. 22, 1989, Pat. No. 5,089,603, which is a continuation-in-part of Ser. No. 369,479, Jun. 21, 1989, Pat. No. 5,079,344.

[51] Int. Cl.$^6$ .................... A61K 39/395; C07K 16/42; C07K 16/28
[52] U.S. Cl. .................... 424/185.1; 530/387.2; 530/388.73; 530/300; 530/350
[58] Field of Search .................... 530/387, 300, 530/350, 387.3, 388.73, 412; 514/12, 2; 424/185.1

[56] References Cited

U.S. PATENT DOCUMENTS 4,636,463  1/1987  Altman et al. .................... 435/7

OTHER PUBLICATIONS

Lawton et al., IgA determinants on B–lymphocytes in patients with deficiency of circulating IgA, J. Lab. Clin. Med., 80(1):26–33, Jul. 1972.

Durkin et al., orignin and fate of IgE–bearing lymphocytes. I. Peyer's patches as differentiation site of cell simultaneously bearing IgA and IgE, J. Exp. Med., 154(3):640–648, Sep. 1981.

Emancipator et al. IgA Immune Complex Renal disease 1983. Annals of the N.Y. Academy of Science vol. 409:171–176. Ed. J.R. McGhee and J. Mestecky.

*Primary Examiner*—David L. Fitzgerald
*Assistant Examiner*—Claire M. Kaufman
*Attorney, Agent, or Firm*—Eric P. Mirabel

[57] ABSTRACT

The invention relates to a method of using a peptide which has the sequence of epitopes which are present on B cell-bound but not secreted IgA. This induces production of the antibody itself. These extracellular peptide segments form, entirely or in part, antigenic epitopes unique to membrane-bound but not secreted IgA.

2 Claims, No Drawings

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( D ) TOPOLOGY: linear ( x i ) SEQUENCE DESCRIPTION: SEQ ID NO:1:

Gly  Ser  Cys  Ser  Val  Ala  Asp  Trp  Gln  Met  Pro  Pro  Pro  Tyr  Val

```
                 1                          5                            10                           15
Val   Leu   Asp   Leu   Pro   Gln   Glu   Thr   Leu   Glu   Glu   Glu   Pro   Gly   Ala   Asn
                              20                            25                           30
```

( 2 ) INFORMATION FOR SEQ ID NO:2:

( i ) SEQUENCE CHARACTERISTICS:
        ( A ) LENGTH: 96 nucleotides
        ( B ) TYPE: Nucleic acid
        ( C ) STRANDEDNESS: double stranded
        ( D ) TOPOLOGY: Linear ( x i ) SEQUENCE DESCRIPTION: SEQ ID NO:2:

```
GGC   TCT   TGC   TCT   GTT   GCA   GAT   TGG   CAG   ATG   CCG   CCT   CCC   TAT   GTG   GTG    48
Gly   Ser   Cys   Ser   Val   Ala   Asp   Trp   Gln   Met   Pro   Pro   Pro   Tyr   Val   Val
 1                       5                            10                           15

CTG   GAC   TTG   CCG   CAG   GAG   ACC   CTG   GAG   GAG   GAG   ACC   CCC   GGC   GCC          93
Leu   Asp   Leu   Pro   Gln   Glu   Thr   Leu   Glu   Glu   Glu   Thr   Pro   Gly   Ala
                        20                            25                           30

AAC   96
Asn
```

( 2 ) INFORMATION FOR SEQ ID NO:3:

( i ) SEQUENCE CHARACTERISTICS:
        ( A ) LENGTH: 26 amino acids
        ( B ) TYPE: amino acid
        ( D ) TOPOLOGY: Linear ( x i ) SEQUENCE DESCRIPTION: SEQ ID NO:3:

```
Glu   Arg   Gln   Glu   Pro   Leu   Ser   Tyr   Val   Leu   Leu   Asp   Gln   Ser   Gln   Asp
 1                       5                            10                           15

Ile   Leu   Glu   Glu   Glu   Ala   Pro   Gly   Ala   Ser
                        20                            25
```

( 2 ) INFORMATION FOR SEQ ID NO:4:

( i ) SEQUENCE CHARACTERISTICS:
        ( A ) LENGTH: 30 nucleotides
        ( B ) TYPE: nucleic acid
        ( C ) STRANDEDNESS: Double stranded
        ( D ) TOPOLOGY: Linear ( x i ) SEQUENCE DESCRIPTION: SEQ ID NO:4:

```
GCGAGAAGTA   CCTGACTTGG   GCATCCCGGC                                                              30
```

( 2 ) INFORMATION FOR SEQ ID NO:5:

( i ) SEQUENCE CHARACTERISTICS:
        ( A ) LENGTH: 17 nucleotides
        ( B ) TYPE: nucleic acid
        ( C ) STRANDEDNESS: Double stranded
        ( D ) TOPOLOGY: Linear ( x i ) SEQUENCE DESCRIPTION: SEQ ID NO:5:

```
CTGCCTGGCC   AAGTCTC                                                                              17
```

( 2 ) INFORMATION FOR SEQ ID NO:6:

( i ) SEQUENCE CHARACTERISTICS:
        ( A ) LENGTH: 21 nucleotides
        ( B ) TYPE: nucleic acid
        ( C ) STRANDEDNESS: Double stranded
        ( D ) TOPOLOGY: Linear ( x i ) SEQUENCE DESCRIPTION: SEQ ID NO:6:

GAACAAGCTC AGTAGGAAGA                                                          21

(2) INFORMATION FOR SEQ ID NO:7:

(i) SEQUENCE CHARACTERISTICS:
        (A) LENGTH: 18 nucleotides
        (B) TYPE: nucleic acid
        (C) STRANDEDNESS: Double stranded
        (D) TOPOLOGY: Linear (xi) SEQUENCE DESCRIPTION: SEQ ID NO:7:

GCTCCCGCTC AGTACTGG                                                            18

(2) INFORMATION FOR SEQ ID NO:8:

(i) SEQUENCE CHARACTERISTICS:
        (A) LENGTH: 22 nucleotides
        (B) TYPE: nucleic acid
        (C) STRANDEDNESS: Double stranded
        (D) TOPOLOGY: Linear (xi) SEQUENCE DESCRIPTION: SEQ ID NO:8:

CCTCCCTATG TGGTGCTGGA CT                                                       22

(2) INFORMATION FOR SEQ ID NO:9:

(i) SEQUENCE CHARACTERISTICS:
        (A) LENGTH: 7 nucleotides
        (B) TYPE: nucleic acid
        (C) STRANDEDNESS: Double stranded
        (D) TOPOLOGY: Linear (xi) SEQUENCE DESCRIPTION: SEQ ID NO:9:

TTGCAGA                                                                         7

(2) INFORMATION FOR SEQ ID NO:10:

(i) SEQUENCE CHARACTERISTICS:
        (A) LENGTH: 6 nucleotides
        (B) TYPE: nucleic acid
        (C) STRANDEDNESS: Double stranded
        (D) TOPOLOGY: Linear (xi) SEQUENCE DESCRIPTION: SEQ ID NO:10:

AATAAA                                                                          6

(2) INFORMATION FOR SEQ ID NO:11:

(i) SEQUENCE CHARACTERISTICS:
        (A) LENGTH: 7 nucleotides
        (B) TYPE: nucleic acid
        (C) STRANDEDNESS: Double stranded
        (D) TOPOLOGY: Linear (xi) SEQUENCE DESCRIPTION: SEQ ID NO:11:

GGATGGA                                                                         7

(2) INFORMATION FOR SEQ ID NO:12:

(i) SEQUENCE CHARACTERISTICS:
        (A) LENGTH: 7 nucleotides
        (B) TYPE: nucleic acid
        (C) STRANDEDNESS: Double stranded
        (D) TOPOLOGY: Linear (xi) SEQUENCE DESCRIPTION: SEQ ID NO:12:

TTGCAGA                                                                         7

( 2 ) INFORMATION FOR SEQ ID NO:13:

( i ) SEQUENCE CHARACTERISTICS:
        ( A ) LENGTH: 7 nucleotides
        ( B ) TYPE: nucleic acid
        ( C ) STRANDEDNESS: Double stranded
        ( D ) TOPOLOGY: Linear ( x i ) SEQUENCE DESCRIPTION: SEQ ID NO:13:

TGGCAGG       7

( 2 ) INFORMATION FOR SEQ ID NO:14:

( i ) SEQUENCE CHARACTERISTICS:
        ( A ) LENGTH: 65 amino acids
        ( B ) TYPE: amino acid
        ( D ) TOPOLOGY: Linear ( x i ) SEQUENCE DESCRIPTION: SEQ ID NO:14:

```
Asp Trp Gln Met Pro Pro Pro Tyr Val Val Leu Asp Leu Pro Gln Glu Thr
 1               5                  10                  15
Leu Glu Glu Glu Thr Pro Gly Ala Asn Leu Trp Pro Thr Thr Ile Thr Phe
        20                  25                  30
Leu Thr Leu Phe Leu Ile Ser Leu Phe Tyr Ser Thr Ala Leu Thr Val Thr
 35              40                  45                      50
Ser Val Arg Gly Pro Ser Gly Asn Arg Glu Gly Pro Gln Tyr
                55                  60                  65
```

( 2 ) INFORMATION FOR SEQ ID NO:15:

( i ) SEQUENCE CHARACTERISTICS:
        ( A ) LENGTH: 71 amino acids
        ( B ) TYPE: amino acid
        ( D ) TOPOLOGY: Linear ( x i ) SEQUENCE DESCRIPTION: SEQ ID NO:15:

```
Gly Ser Cys Ser Val Ala Asp Trp Gln Met Pro Pro Pro Tyr Val Val Leu
 1               5                  10                  15
Asp Leu Pro Gln Glu Thr Leu Glu Glu Thr Pro Gly Ala Asn Leu Trp
        20                  25                  30
Pro Thr Thr Ile Thr Phe Leu Thr Leu Phe Leu Ile Ser Leu Phe Tyr Ser
 35              40                  45                      50
Thr Ala Leu Thr Val Thr Ser Val Arg Gly Pro Ser Gly Asn Arg Glu Gly
                55                  60                  65
Pro Gln Tyr
        70
```

( 2 ) INFORMATION FOR SEQ ID NO:16:

( i ) SEQUENCE CHARACTERISTICS:
        ( A ) LENGTH: 65 amino acids
        ( B ) TYPE: amino acid
        ( D ) TOPOLOGY: Linear ( x i ) SEQUENCE DESCRIPTION: SEQ ID NO:16:

```
Asp Trp Gln Met Pro Pro Pro Tyr Val Val Leu Asp Leu Pro Gln Glu Thr
 1               5                  10                  15
Leu Glu Glu Glu Thr Pro Gly Ala Asn Leu Trp Pro Thr Thr Ile Thr Phe
        20                  25                  30
Leu Thr Leu Phe Leu Ile Ser Leu Phe Tyr Ser Thr Ala Leu Thr Val Thr
 35              40                  45                      50
Ser Val Arg Gly Pro Ser Gly Lys Arg Glu Gly Pro Gln Tyr
```

( 2 ) INFORMATION FOR SEQ ID NO:17:

( i ) SEQUENCE CHARACTERISTICS:
        ( A ) LENGTH: 71 amino acids
        ( B ) TYPE: amino acid
        ( D ) TOPOLOGY: Linear ( x i ) SEQUENCE DESCRIPTION: SEQ ID NO:17:

```
Gly Ser Cys Cys Val Ala Asp Trp Gln Met Pro Pro Pro Tyr Val Val Leu
1               5                   10                  15
Asp Leu Pro Gln Glu Thr Leu Glu Glu Thr Pro Gly Ala Asn Leu Trp
            20                  25                  30
Pro Thr Thr Ile Thr Phe Leu Thr Leu Phe Leu Ile Ser Leu Phe Tyr Ser
35                      40                  45                  50
Thr Ala Leu Thr Val Thr Ser Val Arg Gly Pro Ser Gly Lys Arg Glu Gly
                55                  60                  65
Pro Gln Tyr
        70
```

( 2 ) INFORMATION FOR SEQ ID NO:18:

( i ) SEQUENCE CHARACTERISTICS:
        ( A ) LENGTH: 65 amino acids
        ( B ) TYPE: amino acid
        ( D ) TOPOLOGY: Linear ( x i ) SEQUENCE DESCRIPTION: SEQ ID NO:18:

```
Glu Arg Gln Glu Pro Leu Ser Tyr Val Leu Leu Asp Gln Ser Gln Asp Thr
1               5                   10                  15
Leu Glu Glu Glu Ala Pro Gly Ala Ser Leu Trp Pro Thr Thr Val Thr Phe
            20                  25                  30
Leu Thr Leu Phe Leu Ile Ser Leu Phe Tyr Ser Thr Ala Leu Thr Val Thr
35                      40                  45                  50
Thr Val Arg Gly Pro Phe Gly Ser Lys Glu Val Pro Gln Tyr
                55                  60                  65
```

( 2 ) INFORMATION FOR SEQ ID NO:19:

( i ) SEQUENCE CHARACTERISTICS:
        ( A ) LENGTH: 28 amino acids
        ( B ) TYPE: amino acid
        ( D ) TOPOLOGY: Linear ( x i ) SEQUENCE DESCRIPTION: SEQ ID NO:19:

```
Asp Trp Gln Met Pro Pro Pro Tyr Val Val Leu Asp Leu Pro Gln Glu Thr
1               5                   10                  15
Leu Glu Glu Glu Thr Pro Gly Ala Asn Leu Lys
            20                  25
```

METHOD OF PRODUCING AN ANTIBODY WITH A PEPTIDE CORRESPONDING TO MEMBRANE-BOUND IGA

RELATED APPLICATIONS

This application is a divisional of application Ser. No. 07/455,080, filed Dec. 22, 1989, now U.S. Pat. No. 5,089,603, which is a continuation-in-part of Serial No. 07/369,479 filed Jun. 21, 1989, now U.S. Pat. No. 5,079,344. Priority is claimed to both these applications.

FIELD OF THE INVENTION

The invention relates to a method of treating an infectious disease through administering a peptide with a sequence which corresponds to epitopes which are present on B cell-bound but not secreted IgA.

BACKGROUND OF THE INVENTION

B lymphocytes produce five classes of immunoglobulins, which mediate different functions. IgM is most effective in complement fixation, IgG causes opsonization and cellular cytotoxicity and can cross the placenta. IgA functions on the mucosal surface and IgE mediates degranulation of mast cells and basophils. The function of IgD is still not well understood. These antibodies are present in the blood circulation, with IgG, IgA, and IgM being the major serum components.

In addition to secreting immunoglobulins, the B cells also express different isotypes of the immunoglobulins on their cell surfaces at different stages of maturation. IgM and IgD are present on the surface of resting, uncommitted B cells, while often only one of the five classes of immunoglobulins may exist on late stage, mature B cells, which secrete the same immunoglobulin isotype as expressed on their cell surface. Teale, J.M., et al., *J. Immunol.* 1126:1952–1957 (1981); Gathings, W. E., et al., *Immunol. Rev.* 57:107–126 (1981); Teale, J. M., *Fed. Proc.* 41:5–9 (1982).

Numerous pathogenic microorganisms, such as bacteria and viruses, enter the body through the respiratory, gastrointestinal, and genitourinary tracts during air inhalation, food and liquid intake, and sexual contact. The potentially allergenic substances, e.g., tree, grass, and flower pollens, dust mites, fungal particles and animal dander, also enter the body through the respiratory tract. Secretory IgA antibodies help to defend against these pathogens and allergens.

IgA is produced by plasma cells located along the mucosal linings of the aforementioned tracts, which are all exposed to the external environment. The $\alpha$ chain and light chain immunoglobulins produced by plasma cells combine with a secretory component produced by the epithelial cells in the mucosal tissues, forming secretory IgA molecules that are secreted to the surface of mucosal layers. See generally J. G. Nedrud et al., "Adjuvants and the Mucosal Immune System", *Topics in Vaccine Adjuvant Research*, (Spiggs, D. E., Koff, W. C., Eds.) CRC Press, Boca Raton, Fla. (1990). These secretory IgA molecules bind to the invading pathogens and weaken their ability to penetrate the mucosal layer and to enter the inner tissue and blood stream of the host. See generally J. G. Nedrud et al., "Adjuvants and the Mucosal Immune System", *Topics in Vaccine Adjuvant Research*, (Spiggs, D. E., Koff, W. C., Eds.) CRC Press, Boca Raton, Fla. (1990). IgA can also bind allergenic substances, thereby preventing the allergens from binding IgE or activating the T cells responsible for delayed-type hypersensitivity.

It has been found that individuals with low IgA production are more prone to various infectious diseases and have a higher tendency to develop allergic diseases than those with normal IgA levels. Thus if the levels of either total IgA or antigen-specific IgA can be increased, the diseases or allergies may be prevented.

It is also well known that various allergenic substances enter through inhalation and food ingestion, causing immediate-type, antibody-mediated hypersensitivities and delayed-type, cell-meditated hypersensitivities. In sensitized individuals, the IgE-mediated reactions against pollens, animal danders, dust mites, and other allergenic antigens cause the common allergic symptoms, such as allergic rhinitis ("hay fever") and extrinsic asthma. In such allergic responses, the allergens enter the mucosal layers of the respiratory tracts and nasal linings and bind to allergen-specific IgE which is on the surface of basophils and mast cells. The binding of IgE by the allergens on the basophils and mast cell surface causes cross-linking of the underlying IgE Fc receptors, and triggers the release of histamines and other pharmacologic mediators, resulting in various allergic symptoms. In the cell-mediated hypersensitivities, certain T helper cells responsible for delayed-type hypersensitivity are activated. These T cells recruit and activate macrophages, causing inflammatory symptoms.

It has been shown that antibodies which bind to epitopes of B cell membrane-bound immunoglobulins can be used to eliminate B cells producing the immunoglobulins. In particular, antibodies specific for the antigenic epitope located on the transmembrane anchoring peptide of B cell membrane-bound (but not secreted) IgE can be used for removing IgE secreted B cells in patients suffering from IgE-mediated allergies, as described the published international PCT/US88/04706 patent application, filed Dec. 29, 1988.

Antibodies that belong to certain immunoglobulin classes and subclasses, such as murine $IgG_{2a}$ and human $IgG_1$, and that bind with an appropriately high affinity to surface antigens of target cells can lyse those target cells. However, as noted above, not all antibodies specific for target cells will cause cytolysis, and some in fact cause isotype switching, proliferation, and increased or decreased antibody production. See Vitetta, E. D., et al., *Immunol. Rev.* 52:211–231 (198); Cooper, M. D., et al., *Immunol. Rev.* 52:29–53 (1980). In numerous studies, polyclonal antibodies have also been shown to induce B cell proliferation. See Sell, S. and Gell, P.G.H., *J. Exp. Med.* 122:423–44 (1965); Kishimoto, T., et al., *J. Immunol.* 115:1179–1184 (1975); Parker, D. C., *Nature* 258:361–363 (1975); Sieckmann, D. G., et al., *J. Exp. Med.* 147:814–829; Pure, E. and Vitetta, E. S., *J. Immunol.* 125:1240–1242 (1980). Unlike antibody-dependent cellular cytotoxicity and complement-mediated cytolysis, this proliferative response does not seem to involve the Fc of the antibodies. It has been shown that F(ab')$_2$ is more effective than whole antibody in inducing the proliferative effect, Vitetta, E. S. et al., *Immunol. Rev.* 52:211–231 (1980), indicating the absence of Fc involvement.

Numerous investigators have studied effects of anti-Ig antibodies on the activity of B cells. A review article, "Effects of anti-immunoglobulin sera on B lymphocyte function", *Immunol. Rev.* Vol. 52, ed. by Moller, G. (1980), states that anti-Ig antibodies have a variety of effects on B cells, including the ability to cause proliferation of B cells. In addition, anti-IgM and anti-IgD antibodies appear to be able to switch the resting uncommitted B cells to producers of IgG and IgA. These studies show that divalent antibodies which cross-link the surface Ig are required to stimulate B cell proliferation. These effects do not require Fc portions of the antibodies and, in fact, the F(ab')$_2$ fragments appear to be more effective than whole IgG in stimulating B cell proliferation.

Proliferating B cell with anti-Ig antibodies seem highly desirable for enhancing antibody production in vivo. However, proliferation is difficult to achieve. Because of the large concentrations of IgG, IgM, and IgA antibodies in the circulation, anti-Ig antibodies which are administered will bind to the circulating Ig before they can bind to significant amounts of the surface Ig on B cells. What is needed is a B cell proliferative agent which reacts with membrane-bound immunoglobulins and causes proliferation or B cell modulation without reacting with the secreted, circulating immunoglobulins.

SUMMARY OF THE INVENTION

The invention includes the membrane anchoring peptide of human a chain, antibodies and related products to epitopes on the extracellular segment of this peptide, and prophylactic and therapeutic treatments involving such antibodies and related products. These extracellular peptide segments form, entirely or in part, antigenic epitopes unique to membrane-bound but not secreted IgA.

The membrane anchoring extracellular peptide segment for human IgA has the amino acid sequence: SEQ ID NO:1, wherein the fourth Serine residue can be substituted with a Cysteine.

Peptides including this sequence or an immunologically equivalent sequence (or a epitope thereof) can be conjugated to protein carriers and used to induce formation of endogenous antibodies to these unique extracellular epitopes of human IgA. These endogenously produced antibodies modulate the synthesis of IgA and, in particular, increase its synthesis. When the antibodies specific for these extracellular epitopes are of certain immunoglobulin classes and subclasses, such as mouse IgG$_1$ or human IgG$_2$, or in the form of divalent antigen binding fragments such as F(ab')$_2$, they can be administered to directly enhance IgA synthesis. Further, peptides representing IgM or IgD, or antibody specific for these peptides, can be used to stimulate IgA production. The peptides and antibodies can be used alone, or combined with vaccines or allergenic antigens, to increase IgA synthesis. The patient population includes those susceptible to infectious diseases and those affected by allergic diseases.

DETAILED DESCRIPTION OF THE INVENTION AND ITS MANNER AND PROCESS OF MAKING AND USING

1. Membrane Anchoring Peptides of B Cell Membrane-bound Immunoglobulins

The membrane-bound immunoglobulins expressed in the surface of B cells differ from the secretory immunoglobulins synthesized by the same cells in that the former have extra peptidic segments extending from the C-termini of the immunoglobulin heavy chains which anchor the immunoglobulins to the cell surface. These extra segments are unique for different isotypes and are referred to herein as the membrane anchoring peptides.

The amino acid sequence data of the eleven membrane-bound immunoglobulins from several species have been determined. See Word, C. J. et al., *EMBO J.* 2:887–898 (1983); Ishida, N. et al., *EMBO J.*, 1:1117–1123 (1982); Steen, M. L. et al., *J. Mol. Biol.*, 177:19–32 (1984); Rogers, J. et al., *Cell,* 26:19–27 (1981); Yamawaki-Kataoka, Y. et al., *Proc. Natl. Acad. Sci.,* USA, 79:2008–2012 (1982); Kamaromy, M. et al., *Nucleic Acids Res.,* 11:6775–6785 (1983); Rogers, J. et al., *Cell,* 20:303–312 (1980); Bernstein, K. E., *J. Immunol.* 132:490–495 (1984); Cheng, H. et al., *Nature,* 296:410–415 (1982); Robbitts, T. H. et al., *Nucleic Acids Res.* 9:4509–4524. These sequences indicate certain common features of the membrane anchoring peptides. As shown in Table 1, the membrane anchoring peptide has three segments which are distinguishable based upon their locations in relation to the plasma membrane. Even though these peptides are short, ranging from 41 to 130 amino acid residues, and have often been referred to as the "membrane-bound domain", the peptides are not entirely in the membrane lipid bilayer. In fact, only 25 amino acid residues, largely hydrophobic residues and threonine and serine residues which are located in the middle part of the peptides, are in the lipid bilayer. The C-terminal, hydrophilic segments of 3 to 28 amino acid residues are located on the cytoplasmic side of the membrane. The segments toward the N-terminus, which are connected to the third or fourth constant domains of the immunoglobulin heavy chains (CH$_3$ or CH$_4$) are very hydrophilic and are on the extracellular side of the plasma membrane.

TABLE 1

Key Features and Properties of Peptide Segments Unique to Membrane-Bound Immunoglobulins.

| Immuno-globulin Class/Subclass | First Segment | Middle Segment Length # Amino Acid Residues | Last Segment | Total |
|---|---|---|---|---|
| Mouse IgA | 26 | 25 | 14 | 65 |
| Mouse IgE | 19 | 25 | 28 | 72 |
| Rat IgE | 19 | 25 | 28 | 72 |
| Mouse IgG$_1$ | 18 | 25 | 28 | 71 |
| Mouse IgG$_{2a}$ | 18 | 25 | 28 | 71 |
| Mouse IgG$_{2b}$ | 18 | 25 | 28 | 71 |
| Mouse IgG$_3$ | 18 | 25 | 28 | 71 |
| Mouse IgM | 13 | 25 | 3 | 41 |
| Human IgM | 13 | 25 | 3 | 41 |
| Human IgD | 27 | 25 | 3 | 55 |
| Mouse IgD | 26 | 25 | 3 | 54 |
| Properties | Hydrophilic Highly Acidic | Hydrophobic No Charged Residues | Hydrophilic | |
| Physical Location | On Exterior Surface | In Membrane Lipid Bilayer | On Cytoplasmic Surface | |
| Abbreviated Symbols | mb/ec Segment | mb/tm Segment | mb/ic Segment | |

*mb stands for membrane-bound; ec for extracellular; tm for transmembrane; and ic for intracellular.

The shortest extracellular segments of the membrane-bound pieces of the immunoglobulins (designated mb/ec segments) have 13 amino acid residues (mouse and human μ chains). The mb/ec segments of all immunoglobulins contain high proportions of charged, acidic, amino acid residues. The charged amino acid residues and polar hydrophilic residues account for a very high percentage of the amino acids in the mb/ec segment. This indicates that all the mb/ec segments are exposed and of sufficient length to be accessible by antibodies.

2. The Amino Acid Sequence of the mb/ec Segment of Human IgA (α.mb/ec segment)

The DNA sequence corresponding to the human α.mb/ec segment was determined as set forth in the exemplification below. The nucleotide sequence of the exon encoding the peptide segment and the amino acid sequence of the segment are respectively shown in SEQ ID NO:2.

The α.mb/ec peptides include any modifications of the amino acid sequence of SEQ ID NO:1 in which amino acids have been added, inserted, deleted or substituted without detracting significantly from the immunological activity of the peptide. The immunological activity of the peptide includes reactivity with antibody and the ability (alone or conjugated to a carrier) to induce an immune response, including inducing an antibody response which is crossreactive with both the α.mb/ec segment and with native IgA on the cell membrane.

Such immunogenic peptides can be synthesized by conventional techniques, such as with the RAMPs system (DuPont DeNemours & Co.) which applies Fmoc chemistry. Alternatively, these recombinant peptides or immunoglobulin heavy chains containing epitopes of these peptides may be biosynthesized by expressing in *E. coli* or mammalian cells the gene segments containing coding sequences of the peptide.

3. Developing Antibodies to the mb/ec Segment

The α.mb/ec peptide can be used in the immunization of animals to prepare polyclonal and monoclonal antibodies. It can also be used to screen for specific monoclonal antibodies or characterize specific polyclonal antibodies. It can also be used to purify monoclonal and polyclonal antibodies.

In the process of preparing monoclonal antibodies specific for α.mb/ec peptide, it is not necessary to use the synthetic or recombinant α.mb/ec peptides in both immunization and antibody identification. For example, in immunizing mice for preparing immune spleen cells for fusion with myeloma cells, the immunogen may be the membrane-bound IgA isolated from plasma membrane of IgA-bearing myeloma cells, such as DAKIKI lymphoblastoid cells, or it may be the IgA-bearing myeloma cells themselves. Transfectomas, developed by transfecting mouse myeloma cells with genes of human immunoglobulin heavy chains and light chains and which express on their cell surface membrane-bound immunoglobulins, may also be used as immunogens. For initial monoclonal antibody identification following immunization, the aforementioned synthetic peptide conjugated to bovine serum albumin or ovalbumin with the techniques described below are preferably used.

When using the synthetic or recombinant α.mb/ec peptides as immunogens, it is more effective to conjugate them to a protein carrier, for example, hepatitis B surface antigen, core antigen or preferably keyhole limpet hemocyanin (KLH). If the peptidic segment lacks a Lysine residue or if the Lysine residue is in the middle part of the segment, it is desirable to add a Lysine residue at the C-terminal end. Because the N-terminus already has an α-amino group, the modified synthetic peptidic will have two amino groups for linking.

Multiple molecules of peptides can be conjugated to each molecule of the carrier protein. With KLH, a preferred molar ratio for peptide/KLH is 10. The method of conjugation is well established. Cross-linkers such as bis (sulfosuccinimidyl) suberate or disulfosuccinimidyl tartarate (Catalogue #21579, 20591, Pierce Chemical Co., Rockford, Ill.), or preferably glutaraldehyde, can be used.

The immunogen, e.g. the KLH conjugate, can be used to immunize rabbits, goats, rats, or mice to prepare polyclonal antibodies specific for the α.mb/ec peptide. Lymphocytes from the spleen or lymph nodes of immune mice and rats can also be taken to prepare hybridomas secreting monoclonal antibodies specific for the α.mb/ec peptide. A preferred protocol to prepare the monoclonal antibodies is to fuse immune spleen cells of mice with non-secreting mouse myeloma cells, such as NS-1 or SP2/0 cells, using polyethylene glycol.

A preferred immunization procedure for mice is to prime each mouse by injecting 50 μg of the peptide-KLH conjugate in complete Fruend's adjuvant subcutaneously into each mouse. Two and four weeks later, the same amounts of antigen are given subcutaneously in incomplete Freund's adjuvant. After about six weeks, the fourth antigen injection is given intraperitoneally in saline. Mice are sacrificed 4 days after the last injection and the spleens are removed for preparing single cell suspension for fusion with myeloma cells.

A similar protocol can also be used for immunization with other immunogens. For example, a similar protocol can be used where the immunogen is purified native human membrane-bound IgA (having an attached membrane anchoring peptide) isolated from the plasma membrane of IgA-bearing human myeloma cells, such as DAKIKI lymphoblastoid cells, or where the immunogen is recombinant α chain produced by genetically engineered bacteria.

The fusion procedure with polyethylene glycol and other various procedures concerning cloning and hybridoma culturing have been well established. The preferred protocol is the well-known one described, for example, by Hudson, L. and Hay. F. C. (Practical Immunology, 2nd edition, pp. 303–313, 1980, Blackwell Publishing Co., Boston).

The screening of hybridomas for monoclonal antibodies (or the identification of polyclonal antibodies) reactive with α.mb/ec peptide can be performed with an enzyme linked immunosorbent assay (ELISA) using the synthetic or recombinant α.mb/ec peptide as the solid phase antigen. An alternative solid phase antigen is the conjugate of α.mb/ec peptide with a carrier protein different from that used as the immunogen, such as ovalbumin or bovine serum albumin.

Further characterization of the monoclonal and polyclonal antibodies are shown in Table 2. The assays employed in these studies are also indicated. The assays have been described in detail in co-pending U.S. patent application Ser. No. 07/226,421, filed Jul. 29, 1988, the teachings of which are incorporated by reference herein.

TABLE 2

The Reactivity of Antibodies Specific for the α.mb/ec Peptide with Different IgA- Containing Targets

| | Reactivity | Assays |
|---|---|---|
| Synthetic α.mb/ec peptide | + | ELISA |
| Soluble IgA | – | ELISA |
| DAKIKI myeloma cells | + | Immunofluorescence staining |
| IgA-bearing B cells | + | Immunofluorescence staining |
| Cells not expressing surface IgA | – | Immunofluorescence staining |

4. Experiments with Animal Models

The substances and methods are tested on animal model systems. A number of experiments are designed to investigate whether peptides representing mb/ec segments of various immunoglobulins and the antibodies specific for epitopes on these mb/ec segments will enhance the production of immunoglobulins of various isotypes in the animals. The peptides and antibodies relating to a particular isotype may affect the synthesis of several isotypes and subclasses. In the discussion below, we will primarily focus on peptides and antibodies relating to α.mb/ec segment. The purpose of the animal studies is to investigate:

a) Do the peptides and antibodies enhance antibody production?

b) Do the peptides and antibodies enhance secretory IgA production in the mucosal surface?

c) Can the peptides and antibodies be used prophylactically in preventing from infectious diseases?

d) Can the peptides and antibodies be used in patients with immunodeficiency diseases?

e) Can the peptides and antibodies be used in patients to prevent or alleviate symptoms of allergic diseases?

Two of the most relevant systems are the following.

A. Primate model

The monoclonal antibodies specific for human α.mb/ec peptide and their related substances of this invention are tested to determine whether they react with IgA-bearing cells of rhesus monkeys.

A small portion of rhesus monkeys, which have been infected with the nematode, *Ascaris suum,* develop sensitivity to extract of ascaris. When these sensitive monkeys are given spray containing ascaris antigen, they develop breathing problems resembling asthma. Patterson, R., *j. Clini. Invest.* 57:586–593 (1976).

The various compositions of this invention can be examined in the asthma/rhesus monkey model system. The ascaris sensitive monkeys are given the experimental treatment or control treatment and measurements are made to determine:

(a) Do the asthma symptoms associated with ascaris administration decline?

(b) Does the circulating IgA increase?

(c) Does secretory IgA increase in pulmonary lavage?

(d) Does ascaris antigen-specific IgA increase?

(e) Do IgA-bearing B cells in the circulation and the mucosal layer increase?

B. Mouse model system

The α.mb/ec segment of the mouse has already been sequenced. Word, C. J. et al., *EMBO J.* 2:887–898 (1983). The 26 amino acid residue peptide is SEQ ID NO:3.

The peptide is synthesized in several forms, including one that has extra Leu-Lys residues at the C-terminus.

The peptide and its KLH conjugate are used as antigens to immunize rabbits and goats. The anti-sera are collected. The antigen-specific antibodies are purified using column of Sepharose 4B conjugated with the peptide (with Leu-Lys addition) or with peptide linked to ovalbumin or bovine serum albumin. Alternatively, the peptide-KLH conjugate is used to immunize rats and monoclonal antibodies specific for mouse α.mb/ec are developed by procedures described earlier.

Normal mice are injected intravenously or intraperitoneally with the purified antibodies or their related substances. The mice may also be given α.mb/ec peptide-conjugated with KLH to induce active immunization and endogenous production of anti-α.mb/ec antibodies. They can also be actively immunized with a viral antigen, such as one from a rotavirus, in combination with antibody or peptide treatment. The questions to be investigated are:

(a) Does the total IgA in circulation increase?

(b) Does total secretory IgA increase in the intestinal lumen?

(c) Does antigen-specific IgA increase?

(d) Does the number of IgA-bearing B cells in the spleen and Peyer's patches increase?

(e) Can the mice resist better the challenge with live virus?

5. Application of α.mb/ec Peptide and Antibodies Specific for this Epitope in Infectious Diseases, Allergies, and Immunodeficiency Diseases The α.mb/ec peptide and antibodies specific for α.mb/ec epitopes can be used to increase total IgA, secretory IgA, or antigen-specific IgA in humans or other animals (e.g. dogs, cats, and horses). The antibodies can be used therapeutically and prophylactically in several ways.

A. Antibodies specific for IgA-bearing cells.

Antibodies of certain IgG subclasses, such as mouse $IgG_1$ and human $IgG_2$ and $IgG_4$, or F(ab')2 fragments may be used to enhance antibody production. The antibodies can administered as free antibodies (preferably intravenously) to patients in amounts sufficient to induce proliferation of IgA-bearing B cells and thereby increase IgA production.

The antibodies can also be administered nasally. The concentration of IgA-producing B cells is densest on the lining of the nasal channel and respiratory tract. Nasal administration (e.g. by nasal spray) may be used to deliver relatively high concentrations of antibodies into the nasal and respiratory tracts and thus achieve speedier and more effective results. The antibodies can also be administered ocularly.

For therapeutic uses in humans, especially when repeated or long term administration is necessary, less immunogenic antibodies which are either human, humanized, or chimeric are preferred. Human antibodies, or fragments thereof, can be readily produced from human genomic expression libraries (Stratagene Corp., La Jolla, Calif.). Humanized antibodies can be produced by complementarity region grafting, resulting in an antibody with animal-derived antigen-binding regions, the remainder being of human origin. Richmann, L. et al. *Nature* 332:323–327 (1988). Chimeric antibodies comprise a variable or antigen binding (hypervariable or complementarity determining) region derived from an animal antibody, and the remaining regions derived from a human antibody. Methods for producing chimeric (e.g. murine/human) antibodies are well established. Chimeric antibodies can be produced in large quantities. Antibody fragments of the human or chimeric antibodies can also be used. Single chain antibodies can also be employed. Huston, J. S. et al., *PNAS USA* 85:5879–83 (1983).

Immunotherapies employing the antibodies of this invention may be used in combination with conventional vaccination and desensitization immunotherapy. For example, desensitization with allergen may be performed in conjunction with the administration of anti-α.mb/ec antibodies.

B. α.mb/ec Peptide Analogues and Active Immunization Against α.mb/ec Epitope

Even though human α.mb/ec peptide is probably not immunogenic in humans, synthetic or recombinant peptides with the same sequence, or immunological equivalents can be linked to carrier proteins, such as hepatitis B surface antigen core antigen, or KLH, and become immunogenic and capable to induce antibodies that cross react with authentic α.mb/ec epitope. The preferred synthetic or recombinant peptides have the amino acid sequence SEQ ID NO:1, or immunological equivalents as described above. These α.mb/ec peptide conjugates can be administered to patients susceptible to infectious diseases or IgE-mediated allergies. The antibodies induced by this active immunization can achieve the same functions as the antibodies described above in section A.

C. Antiidiotypic Antibodies and Methods of Active Immunization Against α.mb/ec Epitope The α.mb/ec-specific antibodies described thus far can be used to generate paratope-specific, anti-idiotypic antibodies which offer another mode of stimulating IgA production. Antibodies against the paratope of the α.mb/ec-specific antibodies conformationally resemble the epitope for which the anti-IgA antibody is specific, that is, they resemble an α.mb/ec epitope. These anti-idiotypic antibodies (preferably in the form of chimeric or human anti-idiotypes, or fragments thereof, or peptides containing the antigen combining portions thereof) can be administered in an immunogenic quantity to actively immunize against α.mb/ec and induce the endogenous formation of antibodies against the α.mb/ec epitope. The induced antibodies will mediate the various prophylactic and therapeutic effects of α.mb/ec-specific antibodies.

6. Diagnostic Uses

Antibodies against α.mb/ec epitopes can be used for determining numbers and relative proportions of IgA-bearing lymphocytes in mixed leukocyte populations. The α.mb/ec-specific antibodies will not react with cells which bear secreted immunoglobulins on the cells' Fc receptors. Such cells include macrophages and activated T cells. The profile of the IgA-bearing B cells may indicate the immune status of the individual. The same information can indicate how much antibody should be administered to cause proliferation of IgA-expressing B cells. For this purpose, antibodies can be used in standard assay formats which are used to determine cell surface antigens. In general, the antibody is contacted with a sample of the leukocytes to be tested under conditions which allow the antibody to bind IgA-bearing cells in the sample. The cells are then examined for binding of antibody. This can be accomplished by conventional cell staining procedures, for example, a fluorescently labeled second antibody can be used to detect binding of the anti-IgA antibody.

EXAMPLE I: DETERMINING THE SEQUENCES OF α.mb/ec Peptide

MATERIALS AND METHODS

DNA library and probe.

The human genomic DNA library was purchased from Stratagene (La Jolla, Calif.). This library was constructed using genomic DNA from human lung fibroblast line, WI38, packaged in phage FIX. A 30-base oligonucleotide SEQ ID NO:4, which corresponds to a segment located in the CH3 coding region of immunoglobulin allotype α1 and α2, was synthesized and used as a probe to screen phage clones containing either α1 and α2 gene segments using in situ hybridization.

Polymerase chain reaction (PCR).

To amplify genomic DNA segments, the purified DNA from the positive clones was used as the templates. One primer was a 17-base oligonucleotide, SEQ ID NO:5, located in the intron about 1 kb down-stream from CH3 exon, and the other primer was a 21-base oligonucleotide, SEQ ID NO:6, which is a very conservative segment in the published mouse α membrane exon (Word et al. *EMBO J.* 2:887,1983). To amplify cDNA spanning human CH3 and the membrane exon, purified cDNA reverse transcribed from mRNA from a surface IgA-expressing cell line (see below) was used as the template. One primer was the same 30-base oligonucleotide (SEQ ID NO:4) located in CH3 exon used in genomic library screening, and the other primer was an 18-base oligonucleotide, SEQ ID NO:7, which is located at the junction of human a membrane exon and the 3' untranslated region. The PCR was carried out in DNA Thermal Cycler (Perlin Elmer Cetus) and the reaction conditions were: denaturing at 94° C. for 1 minute, annealing at 50° C. for 2 minutes, reacting with Taq polymerase (Perkin Elmer Cetus) at 72° C. for 5 minutes with genomic DNA, or 45 seconds for cDNA. The reaction cycles were 30 for genomic DNA and 40 for cDNA.

Cloning and sequencing.

The products from PCR were extracted with phenol. The newly synthesized DNA segments were blunted by Mung Bean nuclease (United States Biochemicals) and their 5' ends were phosphorylated by polynucleotide kinase (New England Biolabs). The amplified DNA fragments of interest were isolated by agarose gel electrophoresis and ligated into plasmid pUC19 (United States Biochemicals) at the restriction site of Sma 1. After transforming into *E. coli* DH5α (Bethesda Research Laboratories), the amplified plasmids were purified using CIRCLEPREP kit (BI0101). DNA sequences of the inserts were determined by the method of dideoxy sequencing on double stranded DNA with T7 Sequencing Kit (Pharmacia). The membrane exon regions were sequenced on both strands of DNA to minimize errors. An additional step was performed for identifying clones containing inserts of α gene segment amplified by PCR from cDNA. The colonies were hybridized with an oligonucleotide probe of 22 nucleotides, SEQ ID NO:8, located between the two primers used in PCR.

Southern blot and subclone.

As described above, the first genomic DNA segment used for sequencing was obtained by PCR amplification using two primers, the 3'-end primer of which was in the middle of the membrane exon. In order to obtain sequences for the remaining 3'-end of the membrane exon and the 3' untranslated region, gene segments containing these regions were prepared. Purified genomic DNA's from clones containing human α1 and α2 segments were digested with restriction enzyme Ava 1, electrophoresed on 1% agarose gel, and blotted onto nitrocellulose filter according to the standard Southern blot method. A $^{32}$P labelled oligonucleotide located in the membrane exon mentioned above (SEQ ID NO:8) was used as a probe to identify DNA fragments containing segments neighboring the oligonucleotide probe. The positive segments were then isolated and subcloned into pUC 19 at the restriction site Ava 1 and sequenced downstream using the same oligonucleotide used in Southern blot analysis.

RNA and cDNA preparation.

A mIgA-expressing cell line, DAKIKI (ATCC TIB206), was used as the source of mRNA. About $5\times10^7$ cells were harvested for isolation of total RNA using Guanidinium procedure. With the purified RNA as the template, an oligonucleotide at the end of membrane exon as the primer (SEQ ID NO:7), the first strand cDNA was polymerized by the reverse transcriptase AMV (Life Science, Inc.) according to the procedure in the provided instruction manual.

Results: PCR Amplification of α1 and α2 Gene Segments from Genomic DNA and Their Nucleotide Sequences.

Nine phage lambda clones containing human α1 and α2 heavy chain gene segments were identified from the human genomic library. These clones were used directly as the template for PCr with SEQ ID NO:5 and SEQ ID NO:6 as primers. The 5' end primer (SEQ ID NO:5) for the PCR was selected from a segment identical between human α1 and α2 genes located near the 3' end of the published genomic DNA sequences, which ends in an intron about 1.1 kb downstream from CH3. Flanagen, J. G., et al. *Cell* 36:681–688 (1984). Whether the genes belong to α1 and α2 subclasses can be distinguished by subclass-specific sequences immediately downstream from the SEQ ID NO:5 primer. Both α1 and α2 membrane gene segments were identified among our nine lambda genomic clones. Through agarose gel electrophoresis, the products of PCR were separated into 3 bands of DNA segments, 2 major bands of 1.8 kb and 300 bp, respectively, and a minor band of 2.2 kb. The 1.8 kb segment was thought the segment of interest judging by the size of the corresponding segment in the already sequenced murine α gene. This DNA segment was purified from the agarose gel, subcloned, and sequenced.

The sequence of this 1.8 kb fragment indicated that on its 3' end there was a segment of about 120 bp with a sequence which was very homologous with that of a murine α membrane exon. A possible splicing acceptor sequence, SEQ ID NO:9, was identified near the 5' end of this 120 bp segment. Since the 1.8 kb fragment ends in the middle of the membrane exon, the sequences for the remaining membrane exon and the 3' untranslated region were obtained by subcloning and sequencing of additional lambda clones containing segments flanking the membrane exons. These clones were identified by Southern blot analysis using a probe (SEQ ID NO:8) from the membrane exon.

The sequence of the membrane exon (194 bp) and about 1,700 bp of 5' flanking sequence and about 500 bp in the 3' untranslated region of α1 subclass indicates that the stop codon TGA is at exactly the same site as that of a murine α membrane exon, indicating that human and mouse α membrane exons are both of 194 nucleotides in length. At about 400 bp downstream from the membrane exon, there is a possible mRNA termination and polyadenylation signal sequence, SEQ ID NO:10 (which is part of SEQ ID NO:2). Like the murine α gene, the human α genes have only one membrane exon, while all other classes of human or murine heavy chain genes with known sequences have two membrane exons. The intron between CH3 and the membrane exon has 2,579 bp, somewhat longer than the 2,350 bp of murine. In this intron, there is a region of about 630 bp in which only a few C bases and more than 20 repeated sequences of SEQ ID NO:11 and other repeated sequences exist. The significance of this is unknown.

PCR and DNA sequencing on cDNA.

As mentioned above, the human α membrane exon was located by comparing the sequence of the segment amplified from genomic DNA with that of murine α membrane exon as well as by searching for the splicing acceptor consensus sequence. A segment of 194 nucleotides was originally thought to be the membrane exon. To confirm this, we isolated the total RNA from a human mIgA-expressing cell line, DAKIKI, and prepared its cDNA. With this cDNA as template, a segment spanning CH3 and the membrane exon was amplified by PCR. Although we increased the PCR cycles from 30 to 40, the efficiency of amplification was still not as good as that of PCR on genomic DNA, probably because of the relative lower proportion of the specific template of interest in the cDNA prepared from the total RNA. On agarose gel electrophoresis, the PCR products displayed a weak band of the right size with a heavy smear around it. This band was cut out and subcloned. To help in identifying the specific clones, in situ colony hybridization was performed using a probe located between the two primers of PCR. Positive clones were picked up, purified and sequenced, using the same method as that used for the genomic DNA sequencing.

The results showed that there were clones containing DNA inserts which correspond to two species of mRNA of human membrane-bound α1. The two mRNA species resulted from the use of two different splicing acceptor sites: one from the predicted site, SEQ ID NO:12 which corresponding site existed in the murine α gene; and one from an acceptor site, SEQ ID NO:13, 18 nucleotides upstream in the same reading frame, for which there is not a corresponding site in the murine α gene (the slashes indicate the cleavage/splicing sites). The two mRNA species would yield two membrane-bound α1 polypeptides, one with 65 amino acid residues (SEQ ID NO:14) and the other with 71 amino acid residues (SEQ ID NO:15) in the membrane anchoring peptide region. These two mRNA species and their corresponding α1 peptides are referred to as isoforms.

The proposed extracellular segments of the membrane anchoring peptides of these two isoforms are respectivity either 25 or 31 amino acid residues in length (designated α.mb/ec). These segments are proposed to be extracellular based on the fact that they contain high proportions of acidic residues. These α.mb/ec-α1 segments are the target antigenic epitopes for antibody-based treatments, and are underlined in SEQ ID NOS:14 and 15.

SEQ ID NO:16 shows the amino acid sequence of the shorter isoform (corresponding to SEQ ID NO:14) of human α2, and SEQ ID NO:17 shows the amino acid sequence of the longer isoform (corresponding to SEQ ID NO: 15) of human α2. SEQ ID NO:18 shows the amino acid sequence of the murine a membrane exon.

It can be seen that human α1 and α2 are highly homologous to murine α. Further, the human α.mb/ec peptides are identical between α1 and α2 for isoform 1 and are only one amino acid residue different for isoform 2.

EQUIVALENTS

Those skilled in the art will recognize, or be able to ascertain using no more than routine experimentation, many equivalents to the specific embodiments of the invention described above. Such equivalents are encompassed by the following claims.

What is claimed is:

1. A method of using a peptide which includes an amino acid sequence which is the same as the extracellular segment of the membrane-bound domain of IgA or an epitope thereof, said method comprising immunizing an animal with said peptide to produce an antibody which binds specifically to the extracellular segment of the membrane-bound domain of human IgA on the surface of B-cells and which antibody does not bind to secreted, soluble IgA, and isolating said antibody.

2. A method of using a peptide which includes the amino acid sequence of SEQ ID NO:1 or an epitope thereof, comprising immunizing an animal to produce antibodies which binds specifically to the extracellular segment of the membrane-bound domain of human IgA on the surface of B-cells and which antibody does not bind to secreted, soluble IgA, and isolating said antibody.

* * * * *